United States Patent [19]

Kvalo

[11] Patent Number: 4,828,549
[45] Date of Patent: May 9, 1989

[54] OVER-THE-NEEDLE CATHETER ASSEMBLY

[75] Inventor: Michael M. Kvalo, Safety Harbor, Fla.

[73] Assignee: Critikon, Inc., Tampa, Fla.

[21] Appl. No.: 166,780

[22] Filed: Mar. 7, 1988

Related U.S. Application Data

[63] Continuation of Ser. No. 905,598, Sep. 10, 1986, abandoned.

[51] Int. Cl.[4] ............................................. A61M 5/18
[52] U.S. Cl. .................................................. 604/164
[58] Field of Search ............................. 604/164–170, 604/177

[56] References Cited

U.S. PATENT DOCUMENTS

| | | | |
|---|---|---|---|
| 3,094,122 | 6/1961 | Gauthier | 604/164 |
| 3,406,685 | 10/1968 | May | 604/164 |
| 3,540,447 | 11/1976 | Howe | 604/165 |
| 3,782,381 | 1/1974 | Winnie | 604/164 |
| 3,856,020 | 12/1974 | Kovac | 604/169 |
| 4,177,814 | 12/1979 | Knepshield et al. | 604/167 |
| 4,353,369 | 10/1982 | Muetterties et al. | 604/164 |
| 4,511,356 | 4/1985 | Froning et al. | 604/164 |
| 4,629,450 | 12/1986 | Suzuki et al. | 604/164 |
| 4,650,473 | 3/1987 | Bartholomew et al. | 604/177 |
| 4,713,057 | 12/1987 | Huttner et al. | 604/164 |

FOREIGN PATENT DOCUMENTS 0139872 5/1985 European Pat. Off. ............ 604/168

Primary Examiner—C. Fred Rosenbaum
Assistant Examiner—Mark F. Colosimo

[57] ABSTRACT

An improved over-the-needle catheter assembly is provided with means for facilitating one-handed separation of the catheter hub from the needle hub. The improvement comprises providing the catheter with a top outside surface presenting a generally smooth surface interrupted by a depression. The depression has a bearing wall for transmitting a force component applied by the finger of a user; such force component having a distal, coaxial direction with respect to the catheter hub.

7 Claims, 3 Drawing Sheets

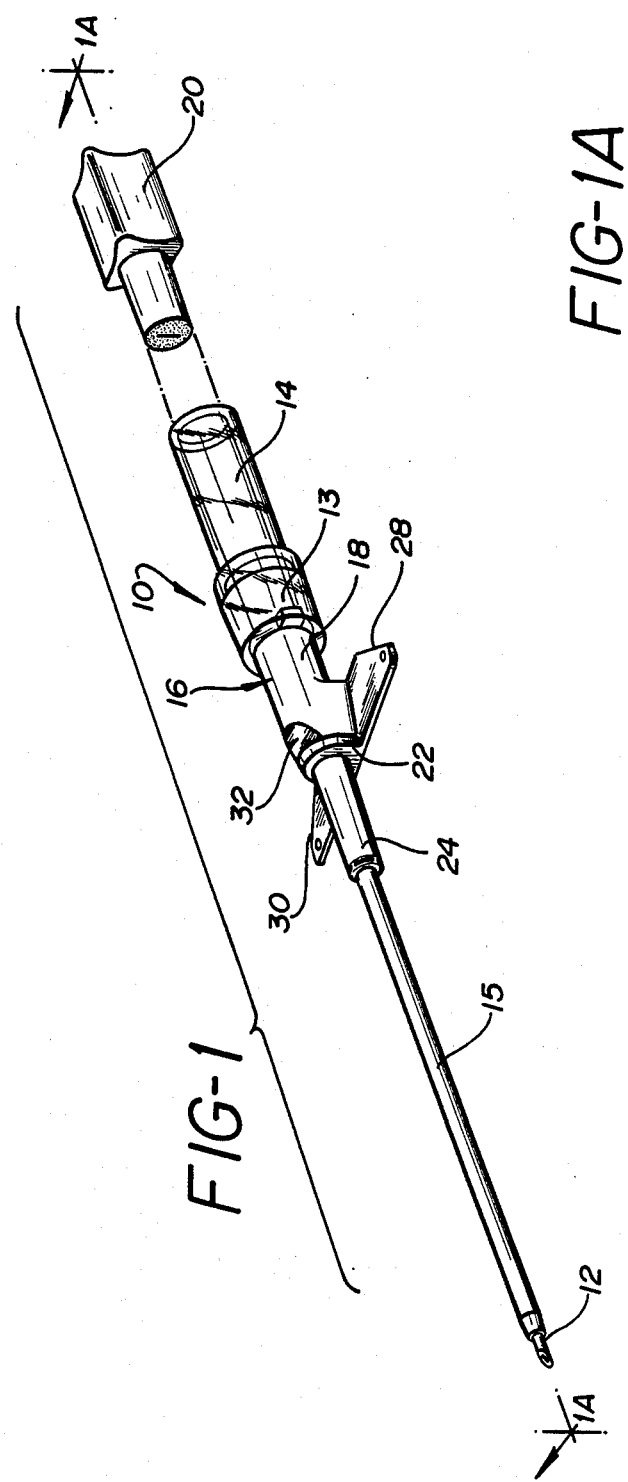
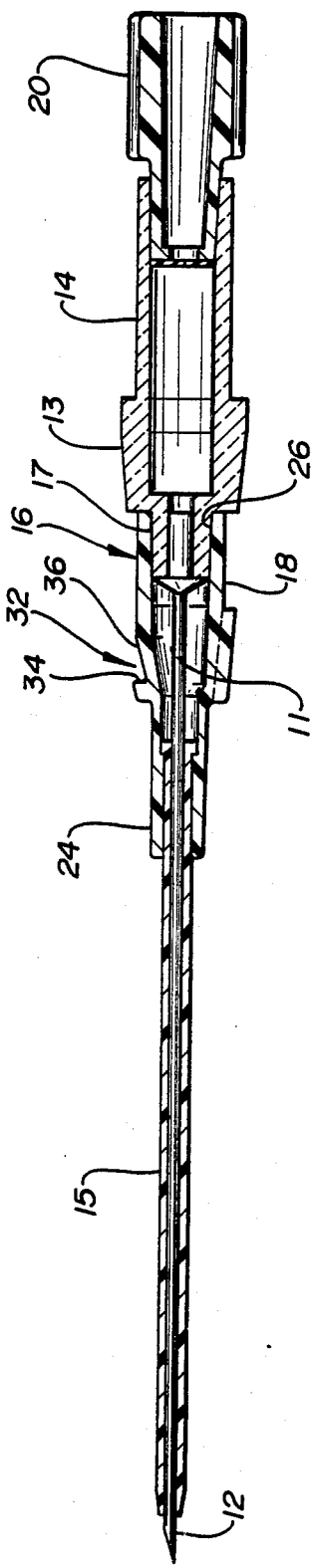

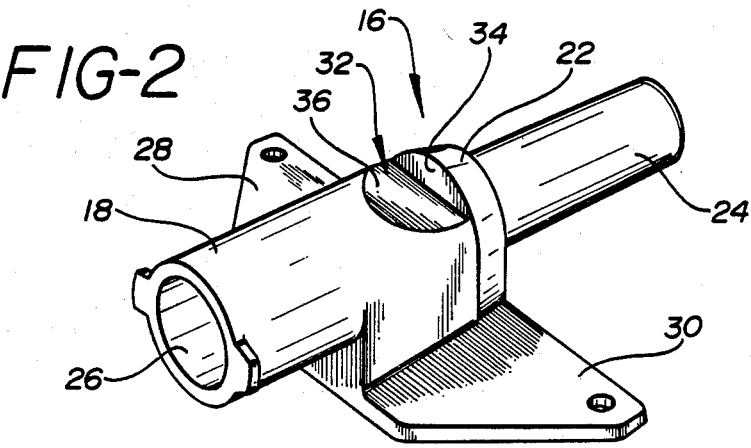
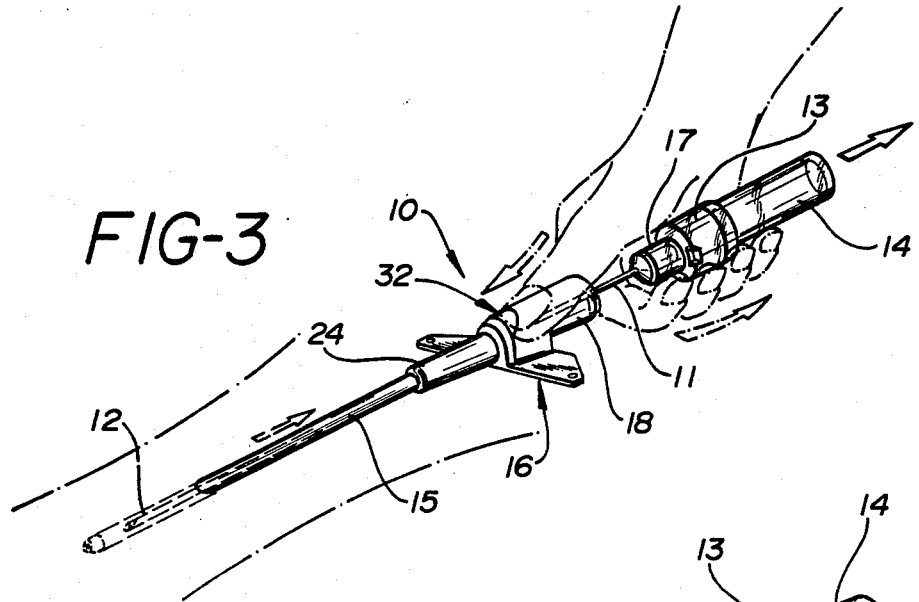
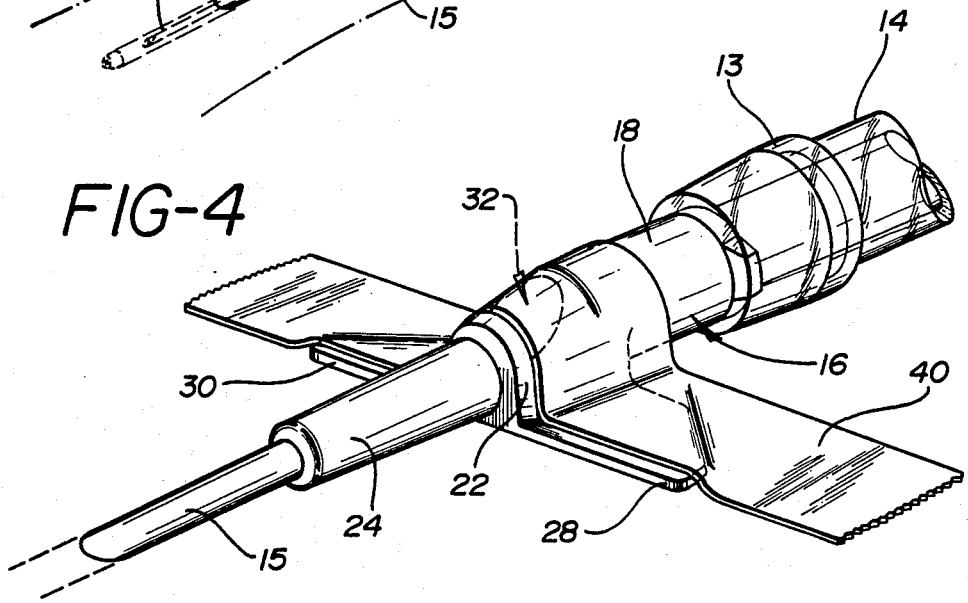

OVER-THE-NEEDLE CATHETER ASSEMBLY

This is a continuation of application Ser. No. 905,598, filed Sept. 10, 1986 now abandoned.

BACKGROUND OF THE INVENTION

This invention relates to catheter assemblies in general and, more particularly, to catheter assemblies known in the art as over-the-needle catheter assemblies.

Such catheter assemblies are now well known and are provided for inserting a catheter into a patient's blood vessel, generally for the purpose of administering fluids therethrough. The catheter generally extends co-axially from the distal end of a catheter hub. The hub, having a lumen therethrough, is open at its proximal end to receive an introducer needle. The introducer needle is inserted through the proximal end of the hub and through the catheter, with the distal end of the needle, usually provided with a sharpened piercing end, protruding from the distal end of the catheter. The proximal end of the needle is generally affixed to a needle hub.

When the assembly is ready to use for inserting the catheter into a patient's blood vessel, the distal end of the needle hub is usually seated into the proximal end of the catheter hub. The piercing end of the needle is employed to pierce the blood vessel and the catheter is then urged distally over the needle and seated into the blood vessel. At this point, the needle is withdrawn from the catheter by separating the catheter hub from the needle hub and withdrawing the needle proximally from the catheter.

Normally, during the process of removing the needle, one hand of the user, e.g., the nurse, is occupied with occluding the patient's blood vessel to prevent excessive blood flow. Accordingly, the removal of the needle and, more difficulty, the separating of the needle hub from the catheter hub, must be accomplished with one hand.

Several techniques have been developed by users for effecting such one handed separation. Most commonly, the thumb, or in some cases another finger of one hand, is placed upon the catheter hub while one or more of the remaining fingers of such hand grips the needle hub. The thumb and gripping fingers are then moved apart to separate the two hubs. Such techniques may be employed with over-the-needle catheter assemblies such as are disclosed in U.S. Pat. No. 3,352,306 to S. Hirsch; U.S. Pat. No. 3,406,685 to E. A. May; Czechoslovakian Pat. No. 77,010 to J. H. Waelsch.

Several prior suggestions have been made for catheter assemblies which will facilitate the one-handed separation of catheter hub from needle hub. Generally, such suggestions employ a projection extending outwardly from the surface of the catheter hub which the thumb, or other digit, may engage to effect separation. Examples of such assemblies with outwardly extending projections are U.S. Pat. No. 3,348,544 to B. Brown; U.S. Pat. No. 3,454,006 to A. J. Langdon; U.S. Pat. No. 3,515,137 to L. S. Santomieri; U.S. Pat. No. 3,595,230 to G. M. Suyeoka, et al; U.S. Pat. No. 3,714,945 to V. F. Stanley; and French Pat. No. 1,534,118 to M. J. Salem.

In providing such outwardly extending projections, two conflicting criteria have rendered prior suggestions less than totally satisfactory. Firstly, it is highly desirable that, when applying a digit to the catheter hub to effect separation, such digit does not contaminate the proximal end of the catheter hub in that it is this surface which will come into contact with the source of fluid to be administered to a patient. It is understood that, after removal of the needle, the catheter hub is connected to a fluid administration means, e.g., an intravenous administration set. Accordingly, it is a desirable criterion that the projection be positioned at the most distal portion of the catheter hub in order to provide sufficient room for the digit to be applied without such digit contaminating the proximal end of the hub.

Secondly, it is equally desirable to have the distal end of the hub present as smooth a surface as is possible. This is to allow the user, after the catheter has been inserted into the patient, to anchor the catheter against the patient's body. Ordinarily this is done with adhesive tape and an outwardly extending projection at the distal end of the hub will interfere with such taping. Accordingly, it is desirable, from the taping point of view, to have the projection located as close to the proximal end of the hub as is possible.

It can thus be seen that the placement of the projection is a compromise between the sterility and taping requirements and any placement is less than totally satisfactory. In fact, it is preferred that no projection be provided were it not for the need to facilitate separation of the hubs. This is because any projection has the potential to snag against an object and cause the catheter to dislodge.

Accordingly, there is a need for providing, in an over-the-needle catheter assembly, improved means for facilitating one handed separation of the catheter hub from the needle hub.

SUMMARY OF THE INVENTION

In accordance with this invention, means are provided in an over-the-needle catheter assembly for facilitating one-handed separation of the catheter hub from the needle hub without the drawbacks of the prior suggestions. Specifically, such means are provided so that a digit may be placed on the catheter hub without danger of contaminating the proximal end thereof and, at the same time, such means do not interfere with the taping of the distal end of the catheter hub.

The invention resides in providing improvements, in an over-the-needle catheter assembly having a catheter depending from the distal end of a catheter hub, the proximal end of said catheter hub adapted to accept a needle hub having a needle extending from the distal end of said needle hub. Such catheter assembly is improved by having the outside surface of said catheter hub present a generally smooth surface interrupted by a depression. The depression has a bearing wall for transmitting a force component applied by the finger of a user; said force component having a distal, coaxial direction with respect to the catheter hub.

In a preferred embodiment, the depression is provided with the bearing wall being a planar wall, said wall lying generally in a plane transverse to the axis of the catheter hub and at the distal end of the depression. It is also preferred that the depression, and in particular, the generally planar wall be located at the distal portion of the catheter hub.

The floor of the depression can simply be planar and may be canted at any convenient angle to the axis of the hub.

It may also be preferred to provide a floor which is concave upward in order to accommodate the convex surface of the user's digit and such shape is likewise contemplated herein. Further, the floor as well as the bearing surfaces, may be provided with friction enhancers, e.g., a roughened surface or molded ridges or the like to facilitate separation.

The preferred shape of the smooth outside surface of the catheter hub is that of a conical section the base of which is at the proximal end of the hub and the apex of which is at the distal end. A cylindrical shape is also quite satisfactory.

BRIEF DESCRIPTION OF THE DRAWINGS

FIG. 1 is a perspective view of an embodiment of the catheter assembly of this invention;

FIG. 1A is a longitudinal cross-sectional view of the catheter assembly illustrated in FIG. 1 and taken along line 1A—1A of FIG. 1;

FIG. 2 is an enlarged perspective view of the catheter hub of the catheter assembly shown in FIG. 1;

FIG. 3 is a schematic view of a user separating the catheter hub from the needle hub of the catheter assembly of FIG. 1;

FIG. 4 is a perspective view of the catheter hub of this invention secured to a patient;

DETAILED DESCRIPTION OF THE INVENTION

Figure 5:
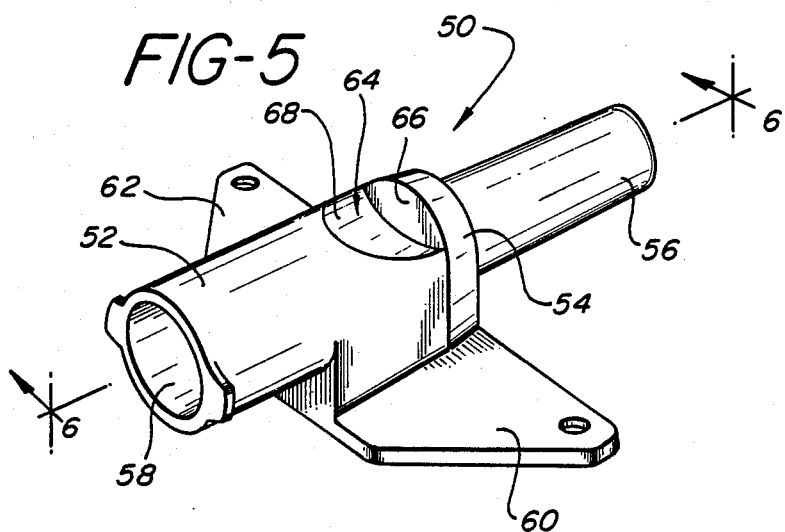
FIG. 5 is a perspective view of an alternative embodiment of a catheter hub of this invention.

Referring now to FIGS. 1, 1A and 2, illustrated therein is a preferred embodiment of the catheter assembly 10 of this invention. The assembly comprises an introducer needle 11 which is in the form of a hollow hypodermic needle having a point 12 on one end thereof. Needle 11 is secured at its blunt end to a needle hub 13 which has a transparent blood detecting chamber 14 integral with its proximal end. The entire hub and blood detecting chamber assembly may preferably be molded in one piece from a suitably clear plastic material e.g. polypropylene, polyacrylate, polycarbonate or styrene butadiene copolymer. Needle 11 serves the function of introducing a flexible polymeric catheter 15 into a blood vessel. Catheter 15 is attached to a catheter hub 16 at its proximal end and hub 16 is adapted to be removably secured to a fitting 17 on the distal end of needle hub 13. A plug 20 is provided for insertion into the proximal end of blood detecting chamber 14 to close such chamber against the passage of blood therefrom.

Referring to FIG. 2, illustrated therein, in enlarged perspective view is a preferred embodiment of the catheter hub 16. The main body of hub 16 has at its top surface (i.e., the surface facing away from the patient's body as distinguished from the surface against the patient's body) the shape of a right conical section 18; the distal end of which is the apex and the proximal end the base. At the distal end, a second conical section 22 is provided having a more acute angle of taper with the base of this second conical section being coextensive with and identical to the apex of the first conical section.

Extending distally from the second conical section is a nose portion 24 into which the proximal end of catheter 15 is affixed. A lumen 26 extends throughout the catheter hub 16 and is aligned for flow communication with the lumen of the catheter 15.

The bottom surface of hub 16 (the surface placed against the patient's body) is flattened and extended transversely into wings 28 and 30 which are employed for providing taping surfaces for taping the catheter hub to the patient after the catheter is emplaced.

In accordance with the teachings of this invention, the distal portion of top surface 10 is smooth and uninterrupted by any upstanding projections of any kind. Instead, as taught herein, the distal portion thereof is provided with a depression 32. The depression 32 is provided with a bearing surface 34 which, as will be described in further detail herein, is for transmitting a force applied by the digit or thumb of the user. In the preferred embodiment illustrated in the drawings, the bearing surface is planar and lies generally in a plane transverse to the axis of the catheter hub 16. The depression 32 is also provided with a floor 36 which is illustrated in its perhaps simplest form as planar and canted at a convenient angle to the axis of the hub. It is important to note that no part of the boundaries of depression 32 project beyond the boundaries of surface 18 and instead, depression 32 may be thought of as being formed by the removal of all material of hub 16 lying above the intersection of planes containing floor 36 and bearing wall 34.

The advantages enjoyed by the catheter assembly embodying the teachings of this invention, as described above, will be understood by consideration of the following description of the assembly's method of use.

As with prior over-the-needle catheter assemblies, to emplace catheter 15, the assembly, as shown in FIGS. 1 and 2 with the needle 11 and plug 20 in place, is employed. The needle 11, with its protruding end 12, is used to pierce the skin and blood vessel of the patient.

At this point in the process the user generally employs one hand to occlude the blood vessel of the patient so as to avoid excess loss of blood. With the other hand, the user must now disengage the distal end of the needle hub 13 from the proximal end of the catheter hub 16 so as to be able to withdraw needle 11 from the catheter 15. The technique employed is illustrated in FIG. 3. As is shown schematically therein, the user applies one digit of one hand (in this case, the thumb) to the catheter hub 16 and with all or some of the remaining digits of the same hand grips the needle hub 13. The one digit and the gripping digits are spread apart to effect separation of the two hubs.

It can now be seen that the depression 32, provided in surface 18 of catheter hub 16, facilitates such use. The one digit may be placed at least partially into the depression 32 and will bear against bearing wall 34 so that the force exerted by the one digit will be transmitted in a direction axially and distally, to the catheter hub 16 so that catheter hub 16 is urged to separate from needle hub 13.

As is shown in the preferred embodiment, the depression and, in particular, the bearing wall 34 is located in the most distal portion of the catheter hub 16, i.e., at the extreme distal end of surface 18. Accordingly, there is no need for the digit to in any way touch or contaminate the proximal end of the catheter hub which end is to be connected to fluid administering means. At the same time, because the bearing wall 34 is created by a depression and because the surface 18 is free of any upwardly extending projection, locating the bearing wall 34 distally does not interfere with the taping of the catheter hub to the patient. As is best illustrated in FIG. 4, catheter 15 is shown emplaced in the patient's blood vessel and the needle 11 and needle hub 13 have been removed. The proximal end of catheter hub 16 may now be placed into flow communication with a source of fluid to be administered and the catheter hub 16 may be anchored in place on the patient's body to avoid dislodgement of the catheter 15. The anchoring is simply accomplished by applying a strip of adhesive tape 40 across the top surface 18 of the catheter hub 16 and beyond the extended wings 28 and 30 onto the patient's body (not shown). Because the depression 32 in no way interferes with the smooth external surface 18 of the catheter hub 16, the tape 40 will lie smoothly against the top surface of the hub, neatly and securely anchoring the catheter hub to the patient.

Figure 6:
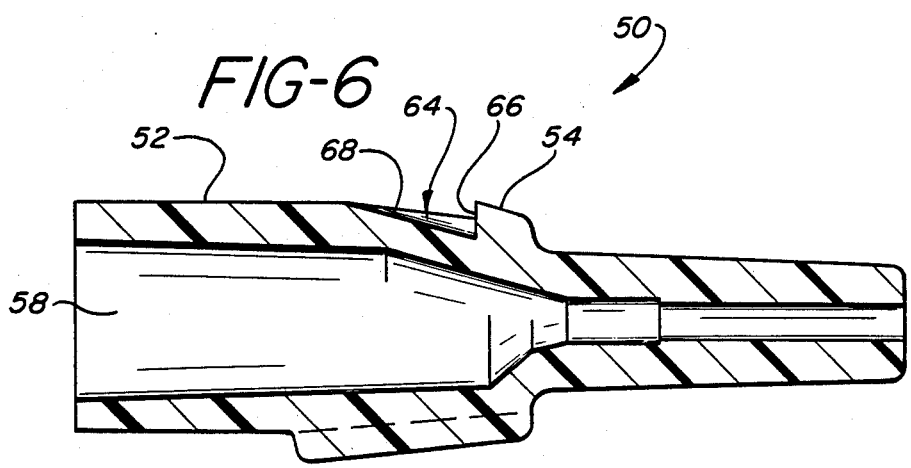
FIG. 6 is a cross-sectional view of the catheter hub of FIG. 5, taken through line 6—6.

It will be appreciated that other shapes for the catheter hub 16 and the depression 32, its bearing wall 34 and its floor 36 are satisfactory while complying with the general teachings of this invention. For example, FIGS. 5 and 6 illustrate, in perspective and longitudinal cross-sectional view respectively, such an alternative embodiment of this invention. Catheter hub 50 is shown with its main body having a top surface 52 in the shape of a conical section. The distal end again is provided with a second conical section 54 tapered at a more acute angle and terminated with a nose portion 56 into which the proximal end of a catheter is affixed. Lumen 58 extends throughout the hub 50. The flattened bottom surface of hub 50 is provided with wings 62 and 60.

A depression 64 is provided in surface 52 at the distal portion thereof. The depression comprises bearing wall 66 and floor 68. Bearing wall 66 is shown planar and transverse to the axis of the hub 50 as in the prior embodiment. On the other hand, the floor 68 instead of being planar, in this embodiment is illustrated as concave upward, complimenting the convex shape of the digit to be applied into the depression 64.

I claim:

1. In an over-the-needle catheter assembly comprising a catheter depending from the distal end of a catheter hub; said catheter hub having a top outside surface on its upper half with respect to the intended location of a patient, and a bottom outside surface on its corresponding lower half for placement against a patient; said catheter hub having a proximal end adapted to accept a needle hub; said needle hub having a distal end and a proximal end and having a needle for accessing a blood vessel extending from the distal end of said needle hub; the improvement wherein said top outside surface of the distal portion of said catheter hub presents a generally continuous surface interrupted by means engageable by a finger for applying a distally directed force to said catheter hub; said finger engageable means comprising a depression located in said upper half of said catheter hub to the exclusion of said lower half and distal the intended location of said needle hub when engaged on said catheter hub; the floor of said depression sloping downward from said continuous surface to define a distal bearing wall therein for transmitting a force component applied by a finger of a user engaged in said depression in the direction of said catheter; whereby said top outside surface distal and proximal said depression provides a substantially continuous taping surface.

2. The catheter assembly of claim 1 wherein said bearing wall is planar and lies in a plane generally transverse to the axis of the catheter hub.

3. The catheter assembly of claim 1 wherein said bearing wall lies at the distal end of said depression.

4. The catheter assembly of claim 1 wherein said depression comprises a planar floor.

5. The catheter assembly of claim 1 wherein such depression comprises a floor which is concave upward.

6. The catheter assembly of claim 1 wherein said top outside surface is the surface of a conical section having a larger base and a smaller base the larger base of which faces the proximal end of said catheter hub and the smaller base of which faces the distal end of said catheter hub.

7. The catheter assembly of claim 1 wherein said top outside surface is the surface of a cylinder.

* * * * *